United States Patent
Garcin et al.

(10) Patent No.: US 6,857,322 B2
(45) Date of Patent: Feb. 22, 2005

(54) METHOD FOR MEASURING COMPRESSIBILITY DURING A POLYMERIZATION PROCESS

(75) Inventors: Alain Garcin, Marignane (FR); Estelle Meurice, St Mitre les Remparts (FR)

(73) Assignee: BP Chemicals Limited, London (GB)

( * ) Notice: Subject to any disclaimer, the term of this patent is extended or adjusted under 35 U.S.C. 154(b) by 36 days.

(21) Appl. No.: 10/240,783

(22) PCT Filed: Apr. 5, 2001

(86) PCT No.: PCT/GB01/01556
§ 371 (c)(1),
(2), (4) Date: Mar. 28, 2003

(87) PCT Pub. No.: WO01/77643
PCT Pub. Date: Oct. 18, 2001

(65) Prior Publication Data
US 2003/0167853 A1 Sep. 11, 2003

(30) Foreign Application Priority Data
Apr. 7, 2000 (FR) .......................................... 00 04495

(51) Int. Cl.[7] .............................................. G01N 3/08
(52) U.S. Cl. ....................................................... 73/818
(58) Field of Search .................... 73/805, 818, 15.6, 73/823, 169, 819, 38; 428/552; 62/54.1; 419/66; 100/37; 424/63; 75/352; 420/8; 106/644, 97

(56) References Cited

U.S. PATENT DOCUMENTS

| 3,750,467 A | * | 8/1973 | Rubio et al. .................. 73/169 |
| 3,847,022 A | | 11/1974 | McGinnis .................. 73/421 R |
| 3,974,679 A | * | 8/1976 | Nasser ........................ 73/15.6 |
| 3,986,566 A | | 10/1976 | Hamilton ...................... 173/31 |
| 4,502,338 A | | 3/1985 | Smith et al. |
| 4,588,443 A | * | 5/1986 | Bache .......................... 106/97 |
| 4,616,508 A | | 10/1986 | Jorn ............................. 73/823 |
| 4,699,011 A | * | 10/1987 | Bradway et al. .............. 73/823 |
| 5,305,646 A | * | 4/1994 | Ashmore et al. ............. 73/818 |
| 5,529,746 A | | 6/1996 | Knöss et al. |
| 5,569,839 A | | 10/1996 | Ajot et al. |
| 5,817,946 A | | 10/1998 | Brovold |

FOREIGN PATENT DOCUMENTS

| EP | 0 360 295 | 3/1990 |
| GB | 2 084 350 | 4/1982 |

OTHER PUBLICATIONS

Yoshiro,; "Method and Device for Powder Compressive Compacting for Evaluating Compressive Compacting Characteristic of Powder"; Patent Abstracts of Japan, of JP 03 291548 A, Dec. 20, 1991.

* cited by examiner

Primary Examiner—Edward Lefkowitz
Assistant Examiner—Octavia Davis
(74) Attorney, Agent, or Firm—Finnegan, Henderson, Farabow, Garrett and Dunner, L.L.P.

(57) ABSTRACT

The present invention relates to a method of measuring the compressibility of a hot powder. In particular, the present invention relates to a method of measuring the compressibility of a polymer hot powder, preferably a polyethylene hot powder.

5 Claims, 3 Drawing Sheets

METHOD FOR MEASURING COMPRESSIBILITY DURING A POLYMERIZATION PROCESS

BACKGROUND OF THE INVENTION

The present invention relates to a method of measuring the compressibility of a hot powder. In particular, the present invention relates to a method of measuring the compressibility of a polymer hot powder, preferably a polyethylene hot powder.

The literature describes methods for measuring the compressibility of a powder. By way of example, mention may be made of the "Johanson Indicizer™ System", a description of the apparatus and the principle of which are described respectively in "Bulk Solids Handling" Vol. 12, No. 2, May 1992, pages 237–240 and in "Part E: Journal of Process Mechanical Engineering", 1996, pages 1 to 8. The major problem encountered with these known methods resides in the difficulty of employing the method in line on an industrial scale as well as the time that is needed to carry it out.

There is therefore a need in the art for a method of measuring the compressibility of a hot powder which is not only easy to implement but is also sufficiently quick to carry out.

The present invention helps to overcome this lack by proposing a measurement of the compressibility of a hot powder which is simple and quick.

SUMMARY OF THE INVENTION

Thus, the present invention relates to a method for measuring the compressibility of a hot powder, characterized in that it comprises the following steps:

- a graduated vertical container is filled with a volume V1 of hot powder, taking care to ensure that the upper surface of this powder volume is plane;
- a piston is placed on this upper powder surface, this piston being guided vertically and sliding freely inside the container and the cross section of the piston having a shape identical to that of the container and being slightly smaller in size;
- the piston is left for a sufficient time to apply its action of compressing the hot powder by the effect of the weight of the piston;
- the volume V2 of hot powder thus compressed is measured with the aid of the graduated container; and
- the compressibility (%) is calculated by means of the equation $$K=((V1-V2)V1)*100.$$

This novel method is particularly advantageous because its simplicity, its quickness and its effectiveness make it also possible to implement it directly in industrial plants, immediately after the powders have been produced, so as to envisage corrective operating measures instantly should there be a deviation in the compressibility properties.

DETAILED DESCRIPTION OF THE INVENTION

Figure 1:
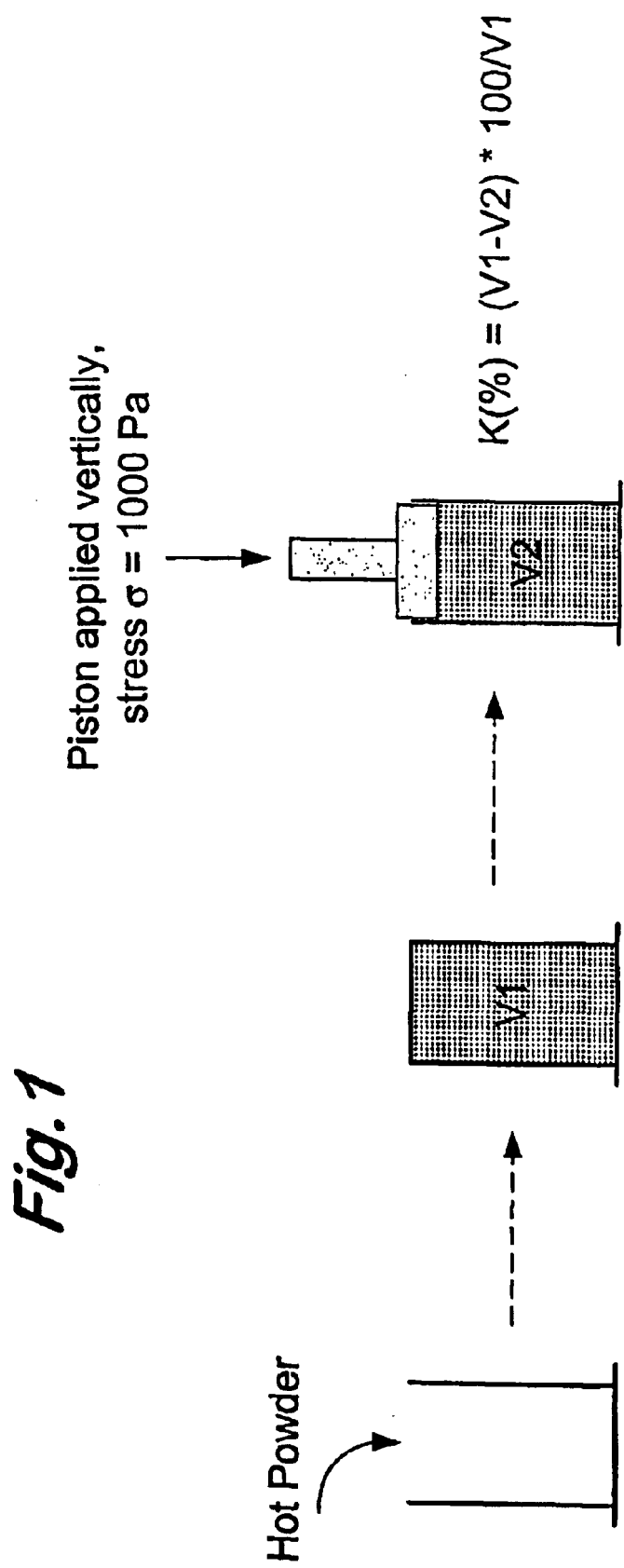
FIG. 1 shows schematically the principle of the compressibility measurement of the hot powder.

While, for the purpose of the present invention, description and appended claims, the term "hot powder" designates a powder showing a temperature that can range from 20 to 150° C., the Applicants have found that this invention is preferably applied when the powder shows a temperature range from 40 to 120° C., preferably from 50 to 100° C., more preferably from 60 to 80° C.

According to an embodiment of the present invention, the piston is left for a sufficient time to apply its action of compressing the hot powder by the effect of the weight of the piston; the ideal timing can easily be determined by the man skilled in the art since it depends mainly on the type of apparatus used and on the powder temperature decrease rate, As per illustrated hereafter, the measurement operation preferably takes between 2 and 15 minutes, more preferably between 4 and 8 minutes.

The Applicant has in fact found that the powder compressibility measurement according to the present invention was directly linked to the flowability property of the said powders; if the flowability becomes poor (which is manifested by a high value of the compressibility K), it is immediately possible to envisage a corrective action which makes it possible to avoid shutting down the industrial plant.

Thus, the present invention also relates to a process for the continuous production of a polymer powder in an industrial plant comprising a reactor for gas-phase polymerization in the presence of a polymerization catalyst, characterized in that at least one operating parameter of the plant is controlled by means of a measurement of the hot powder compressibility K, this compressibility measurement comprising the following steps:

- a graduated vertical container is filled with a volume V1 of hot powder, taking care to ensure that the upper surface of this powder volume is plane;
- a piston is placed on this upper powder surface, this piston being guided vertically and sliding freely inside the container and the cross section of the piston having a shape identical to that of the container and being slightly smaller in size;
- the piston is left for a sufficient time to apply its action of compressing the hot powder by the effect of the weight of the piston;
- the volume V2 of hot powder thus compressed is measured with the aid of the graduated container; and
- the compressibility (%) is calculated by means of the equation.

$$K=((V1-V2)V1)*100.$$

By way of illustration of the polymer powders of interest in the present invention, the following are mentioned:

SBR (a polymer based on butadiene copolymerized with styrene);

ABS (an acrylonitrile-butadiene-styrene polymer);

nitrile (a polymer based on butadiene copolymerized with acrylonitrile);

butyl (a polymer based on isobutylene copolymerized with isoprene);

EPR (an ethylene-propylene polymer);

EPDM (a polymer based on ethylene copolymerized with propylene and a diene such as hexadiene, dicyclopentadiene or ethylidene norbornene);

an ethylene-vinyltrimethoxysilane copolymer, a copolymer of ethylene and of one or more compounds chosen from acrylonitrile, maleic acid esters, vinyl acetate, acrylic and methacrylic acid esters and their homologues.

According to a preferred embodiment of the present invention, it applies to polymers which are preferably polyolefins, particularly copolymers of ethylene and/or of propylene and/or of butene. The preferred alpha-olefin which are used in combination with ethylene and/or propylene and/or butene are those having from 4 to 8 carbon atoms. However, it is also possible to use small amounts of alpha-olefins having more than 8 carbon atoms, for example from 9 to 40 carbon atoms (for example, a conjugated diene).

Preferably, the invention applies to the production of polyethylene, for example linear low-density polyethylene (LLDPE) based, for example, on copolymers of ethylene with 1-butene, 4-methylpentene or hexene, or high-density polyethylene (HDPE) based, for example, on ethylene homopolymers or copolymers of ethylene with small proportions of higher alpha-olefins, for example 1-butene, 1-pentene, hexene or 4-methyl-1-pentene.

Preferably, the present invention relates to the continuous production of polyethylene powder in an industrial plant comprising a gas-phase polymerization reactor of the vertical fluidized-bed reactor type. Preferably, this polymerization is carried out at an absolute pressure of between 0.5 and 6 MPa and at a temperature of between 60° C. and 130° C. For example, in the case of LLDPE production the polymerization temperature is preferably between 75 and 110° C. and in the case of HDPE it is generally between 80 and 120° C. depending on the activity of the catalyst used and on the desired properties of the polymer.

Preferably, the continuous polymerization is carried out in a vertical fluidized-bed reactor in accordance with what is described in the patents (applications) EP-0,855,411, FR No. 2,207,145 or FR No. 2,335,526. The process according to the present invention therefore applies in particular to industrial scale plants, namely, by way of example, to fluidized-bed polymerization reactors whose annual polymer production is at least one hundred thousand tonnes, preferably at least two hundred thousand tonnes.

Preferably, this polymerization is carried out in the presence of a catalytic system of the Ziegler-Natta type, which generally consists of a solid catalyst essentially comprising a compound of a transition metal and a cocatalyst comprising an organic compound of a metal (for example an organometallic compound, for example an alkylaluminium compound). Catalytic systems having a high activity of this type in general comprise a solid catalyst which essentially consists of transition-metal, magnesium and halogen atoms. Ziegler catalysts supported on silica are also appropriate. In particular, it is also possible to use catalysts of the metallocene type as well as iron and/or cobalt complex catalysts, for example those described in WO98/27124 or WO99/12981. It is also possible to use catalysts based on chromium oxide supported on a refractory oxide.

The catalysts may be used as such or in the form of a prepolymer, these being prepared beforehand during a prepolymerization step.

The Applicant has found, quite surprisingly, that it is now possible to avoid crisis situations in industrial plants by using, as a monitoring tool, the measurement of the compressibility K of the polymer powder according to the present invention.

Thus, by way of example, it is used in its industrial plants for the fluidized-bed production of polyethylene, by setting up an analysis of the compressibility of the hot polyethylene powder just after the degasser which is just downstream the outlet of the reactor.

Depending on the grade of polyethylene produced and on its intrinsic characteristics, experience allows one to quickly know, depending on the plant in question, the limiting Klim compressibility value above which the powder would be characterized by a flowability so poor that it would, for example, cause irreversible flow problems. By way of example of corrective actions that may be envisaged when the value of the compressibility approaches too closely the Klim limiting value, mention may be made of an action on the polymerization temperature, on the purging(e.g. with nitrogen) carried out during the degassing, on the aluminium content-admitted into the reactor and on the addition of additives into the polymerization reactor.

As already indicated above, the present invention relates to a method for measuring the compressibility of a hot powder, characterized in that it comprises the following steps:

a graduated vertical container is filled with a volume V1 of hot powder, taking care to ensure that the upper surface of this powder volume is plane;

a piston is placed on this upper powder surface, this piston being guided vertically and sliding freely inside the container and the cross section of the piston having a shape identical to that of the container and being slightly smaller in size;

the piston is left for a sufficient time to apply its action of compressing the hot powder by the effect of the weight of the piston;

the volume V2 of hot powder thus compressed is measured with the aid of the graduated container; and the compressibility (%) is calculated by means of the equation $$K=((V1-V2)V1)*100.$$

By way of indication, the operating principle of the measurement method of the present invention may be illustrated as follows:

a mass equivalent to a force of 1000 Pa is applied to the surface of the powder and the difference in volume occupied by the powder is measured (V1–V2);

an equation M=f*S/g may therefore be written, in which:

M is the mass to be applied, in kg f is the force, in Pa

S is the surface area of the piston in $m^2$ g=9.81 $m/s^2$.

By way of indication, a description of the apparatus that can be used in the present invention may be illustrated as follows:

The apparatus is made of glass and composed of two parts:

1. The piston:
    it measures 77.48 mm in diameter and is hollow in order to be able to be filled with water so as to adjust its mass accurately. It has, in the middle of it, a tube 14.65 mm in diameter so as to guide it vertically and it is held in place by a support It slides freely between the jaws of a clamp.
    It also slides freely inside a glass cylinder of slightly greater diameter, i.e. 79.03 mm, also called the container.

A small cursor, fixed to the piston and corresponding to the bottom of the piston, allows the difference in level on the graduations of the measuring cylinder to be measured directly.

2. The cylinder:

the cylinder, or container, consists of a 2-litre graduated measuring cylinder (1 line=20 ml) and it is cut off at 0.6 litres.

By way of indication, the operating mode according to the present invention may be illustrated as follows:

1. Preparation of the specimen (optional/in principle not applicable if the hot powder is collected directly at the outlet of the reactor or more specifically at the outlet of the degasser):

the powder is mixed, de-aerated and then heated in an oven in order to raise it to 70° C. (the temperature representative of the temperature of the powder in the degasser).

The measuring cylinder is also heated in the oven to the same temperature, i.e. 70° C.

When the powder and the cylinder are at temperature, the powder is again mixed.

2. Measurement:

The cylinder is slowly filled, by pouring the powder until a slope forms above the measuring cylinder, and then the surplus powder in the cylinder is levelled off.

The piston is then placed on the surface of the powder.

With the initial level corresponding to 0.6 litres, the level of the powder on the graduation is read directly after 5 minutes.

It is preferable to carry, out 3 tests and the value $V_2$ (in ml) used for the calculation is the mean of the 3 tests.

Next, the compressibility in % is calculated by means of the equation $$K=((V1-V2)/V1*100.$$

in which V1 is equal to 600 (0.6l initial volume).

The principle of the compressibility measurement is shown schematically by way of indication in FIG. 1.

Figure 2:
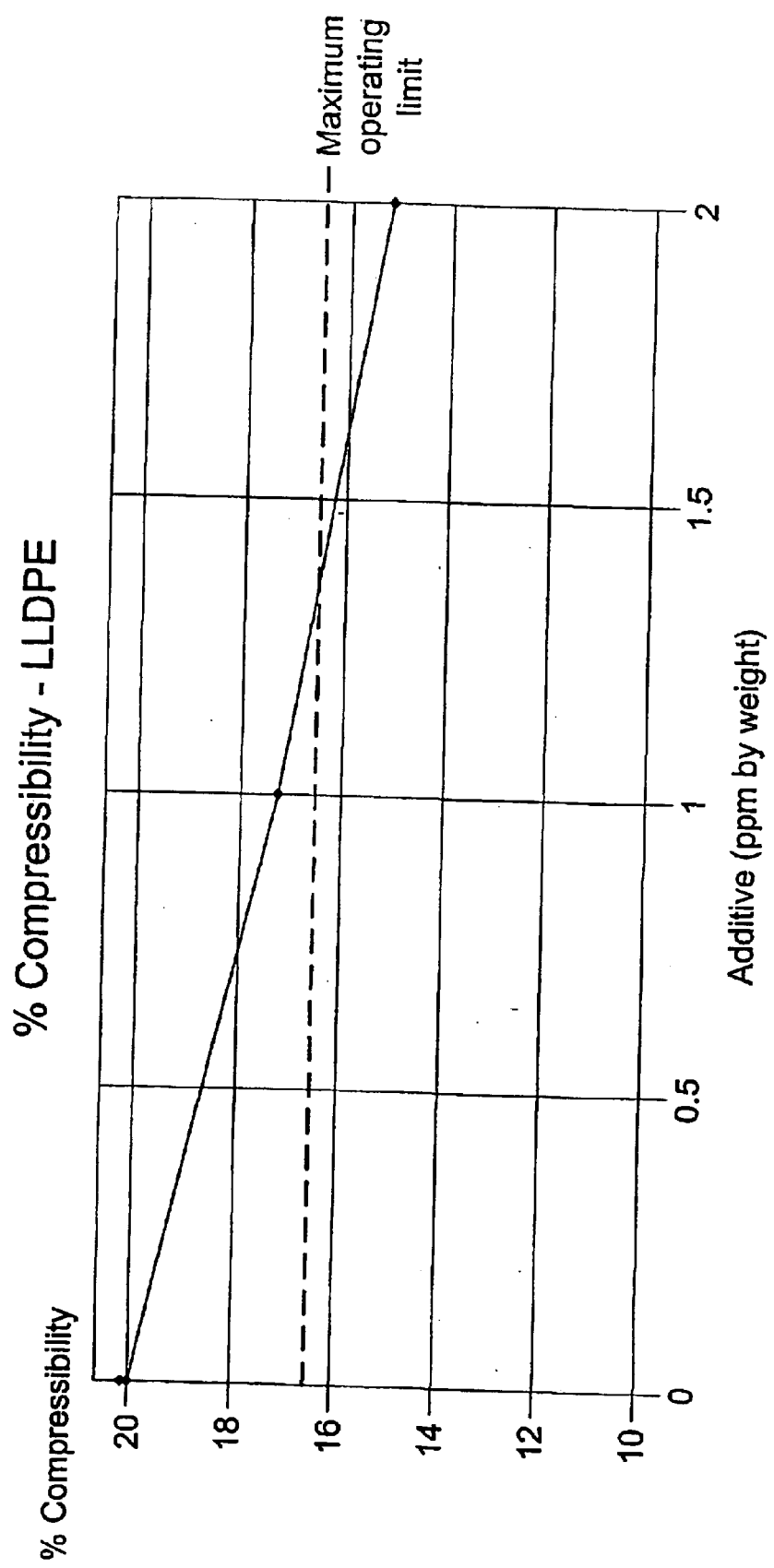
FIG. 2 is a plot of compressibility measurement of hot powder illustrating corrective action taken in the production of a polymer.

By way of example, the plot of the compressibility measurement (FIG. 2) represents a corrective action taken in line in an industrial plant. It portrays an industrial test of the gas-phase polymerization in a plant producing more than 100 thousand tonnes of polyethylene. The catalyst used is a silica-supported catalyst of the type described in Example 1 of Patent Application WO 9513873.

This test is therefore carried out in a vertical fluidized-bed reactor. It is equipped with a fluidization grid in its lower part and comprises a disengagement zone (bulb) in its upper part. An external line for recycling the fluidization gas connects the top of the reactor to the bottom. This line is equipped with a compressor and with a heat exchanger.

The main constituents of the reaction gas mixture are ethylene, hexene and nitrogen.

The polymerization conditions are chosen in such a way as to produce a polyethylene having a density of 0.917 kg/dm$^3$.

A cocatalyst (triethylaluminium) is used at the same time with the catalyst. At the start, (the left part of FIG. 2), a polymer is produced which does not meet the criterion of the present invention since the compressibility value is greater than the limiting value. By an appropriate addition (in this specific case, an addition of Stadis 425 from Octel introduced into the reactor in an amount of 2 ppm by weight with respect to the ethylene/see the right part of FIG. 2), a shutdown of the plant was avoided and powder according to the requirements of the present invention was able to be produced.

Another illustration of the present invention was also performed by using another apparatus as described hereafter:

In this case, a Pressure of 1500 Pa (equivalent mass) is applied on the surface of the hot powder. The bottom part of the apparatus is a cylinder of 600 ml which is filled with hot powder. It is made of Stainless Steel. The internal dimensions are a height of 120 mm and a diameter of 80 mm with graduations every 12.5 ml.

Figure 3:
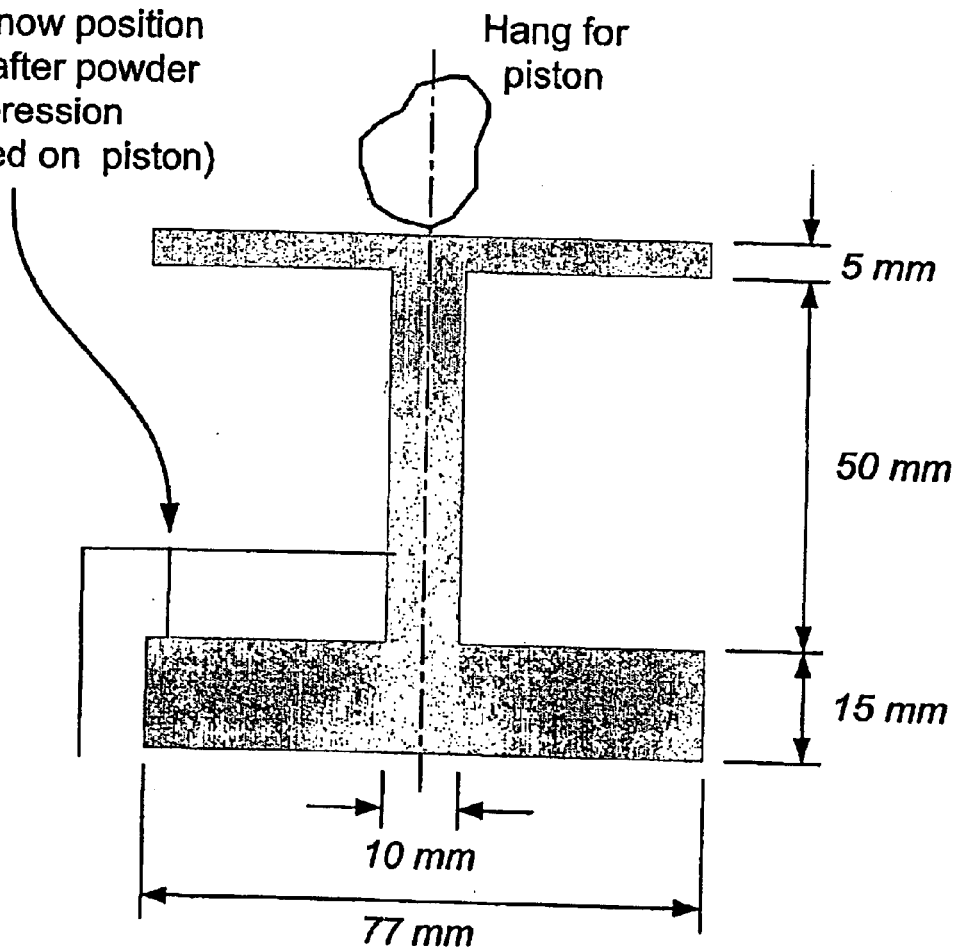
FIG. 3 a schematic view of a device for compressing the hot powder.

Based on "classical" density for Steel: 7800 kg/m$^3$ (from Perry's: Chemical Engineering Handbook), and knowing that a mass of 770 g is necessary to target the 1500 Pa applied on powder, the piston has been dimensioned as described in FIG. 3. When applied on powder, the piston is driven by the piston guide, which is a hollow cylinder, which makes sure that it is horizontal when compressing the hot powder.

What claimed is:

1. A process for the continuous production of a polymer powder, comprising continuously producing a polymer powder in a reactor for gas-phase polymerization in the presence of a polymerization catalyst, and during said production controlling at least one operating parameter thereof by measuring a compressibility value K of a hot powder produced, this compressibility measurement comprising the following steps:

filling a graduated vertical container with a volume V1 of hot powder, so that an upper surface of this powder volume is plane and horizontal;

placing a piston on this upper powder surface, this piston being guided vertically and sliding freely inside the container and the cross section of the piston having a shape identical to that of the container and being slightly smaller in size;

leaving the piston for a sufficient time to compress the hot powder by the effect of the weight of the piston;

measuring a volume V2 of hot powder thus compressed; and calculating the compressibility value K (%) by the equation $K=((V1-V2)/V1)*100$.

2. The process of claim 1, wherein the polymer powder is polyethylene powder.

3. The process of claim 1, wherein the annual production of the polymer powder in the reactor is at least one hundred thousand tonnes.

4. The process of claim 1, wherein a corrective action is taken when a compressibility K value of the polymer powder is greater than or equal to a limiting Klim compressibility value of the polymer powder being produced.

5. The process of claim 4 wherein the corrective action taken is chosen from action on a polymerization temperature, action on a purging with nitrogen carried out during degassing, action on an aluminium content admitted into the reactor or action on an addition of at least one additive into the polymerization reactor.

* * * * *